(12) United States Patent
Bauer et al.

(10) Patent No.: US 7,635,785 B2
(45) Date of Patent: *Dec. 22, 2009

(54) PROCESS FOR PREPARATION OF DIALKYLPHOSPHINIC SALTS

(75) Inventors: Harald Bauer, Kerpen (DE); Werner Krause, Huerth (DE); Martin Sicken, Cologne (DE); Norbert Weferling, Huerth (DE)

(73) Assignee: Clariant Deutschland GmbH, Sulzbach (DE)

( * ) Notice: Subject to any disclaimer, the term of this patent is extended or adjusted under 35 U.S.C. 154(b) by 383 days.

This patent is subject to a terminal disclaimer.

(21) Appl. No.: 11/016,663

(22) Filed: Dec. 17, 2004

(65) Prior Publication Data

US 2005/0137418 A1    Jun. 23, 2005

(30) Foreign Application Priority Data

Dec. 19, 2003    (DE) ................ 103 59 815

(51) Int. Cl.
C07F 9/30    (2006.01)
(52) U.S. Cl. .......................................... 562/8
(58) Field of Classification Search .................... 562/18
See application file for complete search history.

(56) References Cited

U.S. PATENT DOCUMENTS

| | | | |
|---|---|---|---|
| 2,957,931 A | 10/1960 | Hamilton et al. | |
| 3,914,345 A | 10/1975 | Kleiner et al. | |
| 4,036,811 A | 7/1977 | Noetzel et al. | |
| 4,138,433 A | 2/1979 | Kleiner et al. | |
| 5,780,534 A | 7/1998 | Kleiner et al. | |
| 6,013,707 A | 1/2000 | Kleiner et al. | |
| 6,096,914 A | 8/2000 | Seitz | |
| 6,184,405 B1 | 2/2001 | Kleiner et al. | |
| 6,207,736 B1 | 3/2001 | Nass et al. | |
| 6,255,371 B1 | 7/2001 | Schlosser et al. | |
| 6,270,560 B1 | 8/2001 | Kleiner et al. | |
| 6,300,516 B1 | 10/2001 | Weferling et al. | |
| 6,329,544 B1 | 12/2001 | Weferling et al. | |
| 6,355,832 B1 | 3/2002 | Weferling et al. | |
| 6,359,171 B1 | 3/2002 | Weferling et al. | |
| 6,365,071 B1 | 4/2002 | Jenewein et al. | |
| 6,420,459 B1 | 7/2002 | Horold | |
| 6,503,969 B1 | 1/2003 | Klott et al. | |
| 6,534,673 B1 * | 3/2003 | Weferling et al. | 562/8 |
| 6,547,992 B1 | 4/2003 | Schlosser et al. | |
| 6,716,899 B1 | 4/2004 | Klatt et al. | |
| 6,753,363 B1 | 6/2004 | Harashina | |
| 7,087,666 B2 | 8/2006 | Hoerold et al. | |
| 7,148,276 B2 | 12/2006 | Bauer et al. | |
| 7,259,200 B2 | 8/2007 | Bauer et al. | |
| 7,420,007 B2 | 9/2008 | Bauer et al. | |
| 2004/0049063 A1 | 3/2004 | Hoerold et al. | |
| 2005/0009941 A1 | 1/2005 | Sicken et al. | |
| 2005/0101706 A1 | 5/2005 | Bauer et al. | |
| 2005/0143503 A1 | 6/2005 | Bauer et al. | |
| 2006/0074157 A1 | 4/2006 | Bauer et al. | |

FOREIGN PATENT DOCUMENTS

| | | |
|---|---|---|
| DE | 2100779 | 7/1972 |
| DE | 2447727 | 4/1976 |
| DE | 2827867 | 1/1980 |
| DE | 19614424 | 10/1997 |
| DE | 19734437 | 2/1999 |
| DE | 19820398 | 11/1999 |
| DE | 19820399 | 11/1999 |
| DE | 19904814 | 8/2000 |
| DE | 19920276 | 11/2000 |
| DE | 19933901 | 2/2001 |
| DE | 10241373 | 3/2004 |
| EP | 0699708 | 3/1996 |
| EP | 1024167 | 8/2000 |
| EP | 1024168 | 8/2000 |
| EP | 1055676 | 11/2000 |
| EP | 1070754 | 1/2001 |
| EP | 1396522 | 3/2004 |
| EP | 1396524 | 3/2004 |
| EP | 1479718 | 11/2004 |
| EP | 1522551 | 4/2005 |
| EP | 1544206 | 6/2005 |
| WO | WO 96/16948 | 6/1996 |
| WO | WO 98/13371 | 4/1998 |

(Continued)

OTHER PUBLICATIONS

U.S. Appl. No. 11/182,459, by Bauer et al., filed Jul. 15, 2005.

(Continued)

*Primary Examiner*—Paul A Zucker
(74) *Attorney, Agent, or Firm*—Anthony A. Bisulca

(57) ABSTRACT

The invention relates to a process for preparation of salts of dialkylphosphinic acids, which comprises a) reacting hypophosphorous acid and/or its salts with olefins in the presence of a free-radical initiator to give dialkylphosphinic acids and/or their alkali metal salts, in a solvent system, and b) reacting the dialkylphosphinic acids and/or alkali metal dialkylphosphinates obtained in a) with compounds of the metals Mg, Ca, Al, Zn, Ti, Sn, Zr, and/or Fe to give the dialkylphosphinic salts of these metals.

The invention also relates to the use of the metal dialkylphosphinic salts obtained by the inventive process, in particular for preparation of flame retardants.

69 Claims, No Drawings

FOREIGN PATENT DOCUMENTS

| WO | WO 98/08898 | 5/1998 |
|---|---|---|
| WO | WO 98/20012 | 5/1998 |
| WO | WO 98/39381 | 9/1998 |
| WO | WO 98/45364 | 10/1998 |
| WO | WO 99/28327 | 6/1999 |

OTHER PUBLICATIONS

U.S. Appl. No. 11/015,195, by Bauer et al., filed Dec. 17, 2004.
EPO Search Report for EP 04028905, mailed Apr. 11, 2005.
Co-pending U.S. Appl. No. 11/714,482; by Maas et al. filed Mar. 6, 2007.
Co-pending U.S. Appl. No. 11/714,481; by Maas et al. filed Mar. 6, 2007.
Co-pending U.S. Appl. No. 11/714,331; by Maas et al. filed Mar. 6, 2007.
EPO Search Report for EP 04028906, mailed Mar. 16, 2005.
Drinkard, "Some Salts of Symmetric Phosphic Acids", Journal of the American Chemical Society, pp. 5520, 5521 (Nov. 1952).
German Office Action for DE 10359814.6, mailed Aug. 24, 2004.
E.E. Nifante'ev et al., "Journal of General Chemistry USSR" 50(8) pp. 1416-1423(1980).
Office Action for U.S. Appl. No. 11/015,195 dated Jun. 21, 2007.
EPO Search Report for EP 08009495, mailed Jul. 22, 2008.
US 6,248,921, 06/2001, Weferling et al. (withdrawn)

* cited by examiner

PROCESS FOR PREPARATION OF DIALKYLPHOSPHINIC SALTS

The present invention is described in the German priority application No. 103 59 815.4, filed 19 Dec. 2003, which is hereby incorporated by reference as is fully disclosed herein.

The invention relates to a process for preparation of dialkylphosphinic salts, and also to the use of the dialkylphosphinic salts prepared by this process.

Salts of organic phosphorus acids are known as flame retardants. They may be prepared by various processes.

For example, EP-A-0 699 708 describes flame-retardant polyester molding compositions where the polyesters are rendered flame-retardant via addition of the calcium or aluminum salts of phosphinic or diphosphinic acids. The abovementioned salts are obtained via reaction of the corresponding dialkylphosphinic acids with calcium hydroxide or with aluminum hydroxide.

DE 24 47 727 describes flame-retardant polyamide molding compositions which comprise a salt of a phosphinic acid or of a diphosphinic acid.

However, the abovementioned processes have the disadvantage that complicated preparation of the appropriate organophosphorus compounds is first required. This applies in particular to the dialkylphosphinic acids whose aluminum salts give the best results in flame retardant applications, and for which likewise a number of synthetic routes have been described.

For example, DE 21 00 779 A1 describes a process for preparation of alkyl dialkylphosphinates via addition reactions of olefins having from 2 to 22 carbon atoms onto the alkylphosphonous esters, which are obtainable only with difficulty. WO 99/28327 describes a process which starts from alkali metal salts of hypophosphorous acids and gives phosphinic salts in two stages.

That process has the disadvantage of using organic solvents, preferably acetic acid. These have to be recycled in a complicated process and remain as impurities in the final product, leading to undesired side-effects during the intended incorporation into plastics. The use of the organic solvents in the first process stage moreover leads to undesired telomeric by-products, due to the high solubility of the olefin reactants.

An object on which the invention is based is therefore to provide a process for preparation of salts of dialkylphosphinic acids which can prepare, in a particularly simple and cost-effective manner, dialkylphosphinic salts of certain metals with high purity. The intention is to avoid the use of organic solvents.

This object is achieved via a process of the type described at the outset, which comprises a) reacting hypophosphorous acid and/or its salts with olefins in the presence of a free-radical initiator to give dialkylphosphinic acids and/or their alkali metal salts, in a solvent system, and b) reacting the dialkylphosphinic acids and/or alkali metal dialkylphosphinates obtained in a) with compounds of the metals Mg, Ca, Al, Zn, Ti, Sn, Zr, and/or Fe to give the dialkylphosphinic salts of these metals, where the solvent system comprises solvent system additives and water, and where the solvent system comprises from 50 to 100% by weight of water and from 0 to 50% by weight of solvent system additives, preferably from 80 to 100% by weight of water and from 0 to 20% by weight of solvent system additives, and where the solvent additives are mineral acids, acidic salts, carboxylic acids, alkalis, and/or electrolytes, and the mineral acids are element-hydrogen acids, oxo acids, peroxo acids, and/or peroxo diacids of the elements of the seventh, sixth, fifth, fourth, or third main group.

It is preferable that the solvent system comprises from 95 to 100% by weight of water and from 0 to 5% by weight of solvent system additives.

It is preferable that the acidic salts are sodium bisulfate, sodium bisulfite, and/or potassium bisulfite.

It is preferable that the carboxylic acids are formic acid, acetic acid, propionic acid, butyric acid, and/or longer-chain carboxylic acids, and/or their dimers, oligomers, and/or polymers.

It is preferable that the salt of hypophosphorous acid is an alkali metal salt, in particular the sodium salt.

It is preferable that the dialkylphosphinic salts of process stage a) are alkali metal salts, in particular the sodium salts.

It is preferable that the hypophosphorous acid is prepared in situ from salts of hypophosphorous acid and from at least one mineral acid, where the ratio of additive acid to hypophosphite (based on equivalents) is from 0:1 to 2:1.

The reaction in step a) is carried out in the presence of a free-radical initiator.

It is preferable that the free-radical initiators used comprise peroxide-forming compounds and/or peroxo compounds, such as hydrogen peroxide, potassium persulfate, sodium persulfate, ammonium persulfate, and/or azo compounds, such as 2,2'-azobis(2-amidinopropane)dihydrochloride and/or 2,2'-azobis(N,N'-dimethyleneisobutyramidine)dihydrochloride.

It is preferable that the amounts used of the free-radical initiator are from 0.001 to 10 mol %, based on the phosphorus-containing compound.

It is preferable that the free-radical initiator is metered in at a rate of from 0.01 to 10 mol % of initiator per hour, based on the phosphorus-containing compound.

It is preferable that the olefins used comprise ethylene, propylene, n-butene, and/or isobutene, or any desired mixture of these.

It is preferable that the ratio of olefins to hypophosphite and/or hypophosphorous acid (on a molar basis) is from 0:1 to 3:1, preferably from 0.5:1 to 2.5:1.

It is preferable that the reaction in step a) takes place at a pressure of from 1 to 100 bar of the olefin used, preferably from 2 to 50 bar.

It is preferable that the atmosphere in step a) during the reaction is composed of from 50 to 99.9% by weight of constituents of the solvent system and olefin, preferably from 70 to 95% by weight.

It is preferable that the atmosphere comprises gaseous components which do not participate in the reaction.

It is preferable that the gaseous components comprise oxygen, nitrogen, carbon dioxide, noble gases, hydrogen, and/or alkanes.

It is preferable that the reaction in process stage a) takes place at a temperature of from 0 to 250° C., preferably from 20 to 200° C., and particularly preferably from 50 to 150° C.

It is preferable that the reaction in process step a) takes place in absorption columns, spray towers, bubble columns, stirred tanks, and/or kneaders.

It is preferable that the mixer units used comprise anchor stirrers, blade stirrers, MIG stirrers, propeller stirrers, impeller stirrers, turbine stirrers, trough stirrers, disperser discs, cavitation (gasification) stirrers, rotor-stator mixers, static mixers, Venturi nozzles, and/or mammoth pumps.

It is preferable that the reaction solution in process stage a) experiences a mixing intensity corresponding to a rotations Reynolds number of from 1 to 1 000 000, preferably from 100 to 100 000.

It is preferable that in process stage a) the amount of energy introduced during intimate through mixing of olefin, free-radical initiator, the solvent system, and hypophosphorous acid, and/or salts thereof is from 0.083 to 10 kW/m$^3$, preferably from 0.33-1.65 kW/m$^3$.

It is preferable that the reaction of the dialkylphosphinic acids and/or dialkylphosphinic salts with metals and/or metal compounds in process stage b) takes place, for tetravalent metal ions or metals with a stable tetravalent oxidation state, having a molar ratio of dialkylphosphinic acid/dialkylphosphinic salt to metal of from 6:1 to 1:0.66.

It is preferable that the reaction of the dialkylphosphinic acids and/or dialkylphosphinic salts with metals and/or metal compounds in process stage b) takes place, for trivalent metal ions or metals with a stable trivalent oxidation state, having a molar ratio of dialkylphosphinic acid/dialkylphosphinic salt to metal of from 4.5:1 to 1:0.66.

It is preferable that the reaction of the dialkylphosphinic acids and/or dialkylphosphinic salts with metals and/or metal compounds in process stage b) takes place, for divalent metal ions or metals with a stable divalent oxidation state, having a molar ratio of dialkylphosphinic acid/dialkylphosphinic salt to metal of from 3:1 to 1:0.66.

It is preferable that the reaction of the dialkylphosphinic acid and/or dialkylphosphinic salts with metals and/or metal compounds in process stage b) takes place, for monovalent metal ions or metals with a stable monovalent oxidation state, having a molar ratio of dialkylphosphinic acid/dialkylphosphinic salt to metal of from 1.5:1 to 1:0.66.

It is preferable that the metal compounds of Mg, Ca, Al, Zn, Ti, Sn, Zr, or Fe for process stage b) are metals, metal oxides, metal hydroxides, metal oxide hydroxides, metal borates, metal carbonates, metal hydroxocarbonates, metal hydroxocarbonate hydrates, mixed metal hydroxocarbonates, mixed metal hydroxocarbonate hydrates, metal phosphates, metal sulfates, metal sulfate hydrates, metal hydroxosulfate hydrates, mixed metal hydroxosulfate hydrates, oxysulfates, metal acetates, metal nitrates, metal fluoride, metal fluoride hydrates, metal chloride, metal chloride hydrates, metal oxychlorides, metal bromides, metal iodides, metal iodide hydrates, metal derivatives of a carboxylic acid, and/or metal alkoxides.

It is preferable that the metal compounds are aluminum chloride, aluminum hydroxide, aluminum nitrate, aluminum sulfate, titanyl sulfate, zinc nitrate, zinc oxide, zinc hydroxide and/or zinc sulfate.

It is preferable that the reaction in process stage b) takes place at a temperature of from 20 to 250° C., preferably at a temperature of from 80 to 120° C.

It is preferable that the reaction in process stage b) takes place at a pressure of from 1 Pa to 200 MPa, preferably from 0.01 MPa to 10 MPa.

It is preferable that the reaction time of the dialkylphosphinic acids and/or their alkali metal salts with metal compounds of Mg, Ca, Al, Zn, Ti, Sn, Zr, or Fe to give the dialkylphosphinic salts of these metals in process stage b) is from $1*10^{-7}$ to $1*10^2$ h.

It is preferable that the solids content of the dialkylphosphinic salts of the metals Mg, Ca, Al, Zn, Ti, Sn, Zr, or Fe during the reaction of dialkylphosphinic acids and/or their alkali metal salts with metal compounds of these metals to give the dialkylphosphinic salts of these metals in process stage b) is from 0.1 to 70% by weight, preferably from 5 to 40% by weight.

It is preferable that the reaction in process stage b) takes place in a stirred tank, mixer, and/or kneader.

It is preferable that the amount of energy introduced in process stage b) is from 0.083 to 1.65 kW/m$^3$, particularly preferably from 0.33 to 1.65 kW/m$^3$.

It is preferable that in a process stage a1), the dialkylphosphinic acids and/or their alkali metal salts obtained from process stage a) are converted into the respective other group of compounds in order to obtain a uniform product, before process stage b) begins.

It is preferable that alkali metal dialkylphosphinate obtained in process stage a) is converted in a process stage a1) into the dialkylphosphinic acid, and, in process stage b), this is reacted with metal compounds of Mg, Ca, Al, Zn, Ti, Sn, Zr, or Fe to give the dialkylphosphinic salts of these metals.

It is preferable that dialkylphosphinic acid obtained in process stage a) is converted in a process stage a1) into an alkali metal dialkylphosphinate, and, in process stage b), this is reacted with metal compounds of Mg, Ca, Al, Zn, Ti, Sn, Zr, or Fe to give the dialkylphosphinic salts of these metals.

It is preferable that the dialkylphosphinic salts of the metals Mg, Ca, Al, Zn, Ti, Sn, Zr, or Fe from process stage b) are isolated from the reaction mixture via filtration and/or centrifuging.

It is preferable that in process stage b), the diethylphosphinic salt is isolated using pressure filter funnels, vacuum filter funnels, filter funnels with stirrer, pressurized candle filters, axial leaf filters, circular leaf filters, centrifugal leaf filters, chamber/frame filter presses, automatic chamber filter presses, vacuum multicompartment drum filters, vacuum multicompartment leaf filters, vacuum horizontal-table filters, side-feed vacuum filters, rotation pressure filters, vacuum belt filters.

It is preferable that the filtration pressure is from 0.5 Pa to 6 MPa.

It is preferable that the filtration temperature is from 0 to 400° C.

It is preferable that the specific filter rate is from 10 to 200 kg*h$^{-1}$*m$^{-2}$.

It is preferable that the residual moisture level of the filtercake is from 5 to 60%.

It is preferable that the diethylphosphinic salt is isolated in process stage b) using solid-wall centrifuges, such as overflow centrifuges, plough centrifuges, chamber centrifuges, helical-conveyor centrifuges, disc centrifuges, tube centrifuges, sieve centrifuges, such as overdriven centrifuges and underdriven centrifuges, screen-conveyor centrifuges, screen-plough centrifuges, or reciprocating-conveyor centrifuges.

It is preferable that the centrifugal force ratio is from 300 to 15 000.

It is preferable that the suspension throughput rate is from 2 to 400 m$^3$*h$^{-1}$.

It is preferable that the solids throughput rate is from 5 to 80 t*h$^{-1}$.

It is preferable that the residual moisture level of the cake is from 5 to 60%.

It is preferable that after process stage b), diethylphosphinic salt of the metals Mg, Ca, Al, Zn, Ti, Sn, Zr, or Fe isolated from the reaction mixture via filtration and/or centrifuging is dried.

It is preferable that the dialkylphosphinic salt of the metals Mg, Ca, Al, Zn, Ti, Sn, Zr, or Fe has a residual moisture level of from 0.01 to 10% by weight, preferably from 0.1 to 1% by weight.

It is preferable that the dialkylphosphinic salt of the metals Mg, Ca, Al, Zn, Ti, Sn, Zr, or Fe has an average particle size of from 0.1 to 2000 μm, preferably from 10 to 500 μm.

It is preferable that the dialkylphosphinic salt of the metals Mg, Ca, Al, Zn, Ti, Sn, Zr, or Fe has a bulk density of from 80 to 800 g/l, preferably from 200 to 700 g/l.

The invention also provides a process for preparation of dialkylphosphinic salts, which comprises a) reacting hypophosphorous acid and/or its salts with olefins in the presence of a free-radical initiator to give dialkylphosphinic acids and/or their alkali metal salts, in a solvent system, and in a1) converting the dialkylphosphinic acid derivatives obtained in a) mutually into one another.

The invention also provides a process for preparing dialkylphosphinic salts, which comprises a) reacting hypophosphorous acid and/or its salts with olefins in the presence of a free-radical initiator to give dialkylphosphinic acids and/or their alkali metal salts, in a solvent system.

The invention likewise provides a solution of dialkylphosphinic acids and/or of their alkali metal salts, which comprises from 10 to 100% by weight of dialkylphosphinic acids and/or their alkali metal salts
from 10 to 100% by weight of solvent system,
the entirety being 100% by weight.

The invention also provides the use of the dialkylphosphinic salts prepared by the process according to the invention for preparation of flame retardants for thermoplastic polymers, such as polyesters, polystyrene, or polyamide, or for thermosets.

The invention also provides a flame-retardant polymer molding composition comprising the inventively prepared dialkylphosphinic salts of the metals Mg, Ca, Al, Zn, Ti, Sn, Zr, or Fe.

It is preferable that a flame-retardant polymer molding composition comprises from 1 to 50% by weight of inventively prepared dialkylphosphinic salts of the metals Mg, Ca, Al, Zn, Ti, Sn, Zr, or Fe,
from 1 to 99% by weight of polymer or a mixture thereof,
from 0 to 60% by weight of additives
from 0 to 60% by weight of filler.

It is particularly preferable that a flame-retardant polymer molding composition comprises from 5 to 30% by weight of inventively prepared dialkylphosphinic salts of the metals Mg, Ca, Al, Zn, Ti, Sn, Zr, or Fe,
from 5 to 90% by weight of polymer or a mixture thereof,
from 5 to 40% by weight of additives
from 5 to 40% by weight of filler.

The invention also provides polymer moldings, polymer films, polymer filaments, and polymer fibers comprising inventively prepared dialkylphosphinic salts of the metals Mg, Ca, Al, Zn, Ti, Sn, Zr, or Fe.

It is preferable that polymer moldings, polymer films, polymer filaments, or polymer fibers comprise from 1 to 50% by weight of inventively prepared dialkylphosphinic salts of the metals Mg, Ca, Al, Zn, Ti, Sn, Zr, or Fe, from 1 to 99% by weight of polymer or a mixture thereof,
from 0 to 60% by weight of additives,
from 0 to 60% by weight of filler.

It is particularly preferable that polymer moldings, polymer films, polymer filaments, or polymer fibers comprise from 5 to 30% by weight of inventively prepared dialkylphosphinic salts of the metals Mg, Ca, Al, Zn, Ti, Sn, Zr, or Fe,
from 5 to 90% by weight of polymer or a mixture thereof,
from 5 to 40% by weight of additives,
from 5 to 40% by weight of filler.

Finally, the invention also provides dialkylphosphinic salts of the metals Mg, Ca, Al, Zn, Ti, Sn, Zr, or Fe which have a residual moisture level of from 0.01 to 10% by weight, preferably from 0.05 to 1% by weight average particle size of from 0.1 to 1000 μm, preferably from 10 to 100 μm bulk density of from 80 to 800 g/l, preferably from 200 to 700 g/l.

It is preferable that dialkylphosphinic salts of the metals Mg, Ca, Al, Zn, Ti, Sn, Zr, or Fe have been obtained via a process for preparation of these dialkylphosphinic salts in which a) hypophosphorous acid and/or its salts are reacted with olefins in the presence of a free-radical initiator to give dialkylphosphinic acids and/or their alkali metal salts, in a solvent system, and b) the dialkylphosphinic acids and/or alkali metal dialkylphosphinates obtained in a) are reacted with compounds of the metals Mg, Ca, Al, Zn, Ti, Sn, Zr, or Fe to give the dialkylphosphinic salts of these metals.

It is preferable that dialkylphosphinic acids and/or their alkali metal salts have been obtained via reaction of hypophosphorous acid and/or its salts with olefins in the presence of a free-radical initiator to give dialkylphosphinic acids and/or their alkali metal salts in a solvent system.

It is also preferable that dialkylphosphinic acids and/or their alkali metal salts have been obtained via reaction of hypophosphorous acid and/or its salts with olefins in the presence of a free-radical initiator to give dialkylphosphinic acids and/or their alkali metal salts in a solvent system, and then converting the resultant dialkylphosphinic acid derivatives into the respective other group of compounds in order to obtain a uniform product.

It is also preferable that dialkylphosphinic salts have been obtained via a) reaction of hypophosphorous acid and/or its alkali metal salts with olefins in the presence of a free-radical initiator to give dialkylphosphinic acids and/or their alkali metal salts in a solvent system, and then a1) conversion of the dialkylphosphinic acid derivatives obtained in a) into the respective other group of compounds, in order to obtain a uniform product, and then b) reaction of the dialkylphosphinic acid derivatives obtained in a1) with compounds of the metals Mg, Ca, Al, Zn, Ti, Sn, Zr, or Fe to give the dialkylphosphinic salts of these metals.

It is also preferable that dialkylphosphinic salts have been obtained via conversion of alkali metal dialkylphosphinate obtained in process stage a) into the dialkylphosphinic acid and subsequent reaction of this dialkylphosphinic acid with compounds of the metals Mg, Ca, Al, Zn, Ti, Sn, Zr, or Fe to give the dialkylphosphinic salts of these metals.

It is also preferable that dialkylphosphinic salts have been obtained via conversion of dialkylphosphinic acid obtained in process stage a) into alkali metal dialkylphosphinate, and subsequent reaction of this alkali metal dialkylphosphinate with compounds of the metals Mg, Ca, Al, Zn, Ti, Sn, Zr, or Fe to give the dialkylphosphinic salts of these metals.

Surprisingly, it has been found that in an inventive solvent system it is possible to react olefins at a surprisingly good reaction rate, and to suppress greatly the formation of telomeric products, i.e. those which are multiple olefin adducts.

Preferred solvent system additives are mineral acids, e.g. the element-hydrogen acids, oxo acids, peroxo acids, and/or peroxo diacids of the elements of the seventh, sixth, fifth, fourth, or third main group of the Periodic Table.

Particularly preferred mineral acids are hydrofluoric acid, hydrochloric acid, perchloric acid, sulfurous acid, sulfuric acid, peroxomonosulfuric acid (Caro's acid), peroxodisulfuric acid, nitrous acid, nitric acid, phosphorous acid, phosphoric acid, pyrophosphoric acid, polyphosphoric acid, peroxomonophosphoric acid, peroxodiphosphoric acid, carbonic acid, salicic acid, boric acid, peroxoboric acid.

Preferred solvent system additives are alkalis.

Preferred solvent system additives are electrolytes.

The form in which hypophosphorous acid is preferably used is that of aqueous solution and/or anhydrous product.

Preferred cations of the salts of hypophosphorous acid are Li, Na, K, $NH_4$, Tl, Be, Mg, Ca, Sr, Ba, Zn, Cd, Pb, Mn, Ni, Co, Fe, Cu, Al, Cr, Ce, uranyl, Sc, Zr, Hf, Th, Ta, and Ti.

Free hypophosphorous acid is preferably formed in situ from alkali metal hypophosphite and acid. According to the invention, the ratio of acid to hypophosphite (based on acid equivalent) is from 0:1 to 2:1.

An equivalent here is expressed as the fraction calculated from the molar mass of the acid divided by the number of acidic protons.

The olefins preferably bear a functional group.

Preferred functional groups are sulfonic acid, aldehyde, carboxylic acid, carbonyl, hydroxy, thionyl, amino, monoalkylamino, dialkylamino, amino, amido, and nitro.

The olefin used preferably comprises ethylene.

In principle, suitable free-radical initiators are any of the systems which generate free radicals. The olefin addition reaction may be initiated via an anionic initiator or free-radical initiator, or photochemically.

Particularly preferred free-radical initiators are peroxo compounds, such as peroxomonosulfuric acid, potassium persulfate (potassium peroxomonosulfate), Caroate (TM), Oxone (TM), peroxodisulfuric acid, potassium persulfate (potassium peroxodisulfate), sodium persulfate (sodium peroxodisulfate), ammonium persulfate (ammonium peroxodisulfate).

Particular preference is given to compounds which form peroxides in the solvent system, for example sodium peroxide, sodium peroxide peroxohydrate, sodium peroxide diperoxohydrate hydrate, sodium peroxide dihydrate, sodium peroxide octahydrate, lithium peroxide, lithium peroxide monoperoxohydrate trihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Particular preference is given to hydrogen peroxide, performic acid, peracetic acid, benzoyl peroxide, di-tert-butyl peroxide, dicumyl peroxide, 2,4-dichlorobenzoyl peroxide, decanoyl peroxide, lauroyl peroxide, cumene hydroperoxide, pinene hydroperoxide, p-menthane hydroperoxide, tert-butyl hydroperoxide, acetylacetone peroxide, methyl ethyl ketone peroxide, succinic acid peroxide, dicetyl peroxydicarbonate, tert-butyl peroxyacetate, tert-butyl peroxymaleic acid, tert-butyl peroxybenzoate, acetyl cyclohexylsulfonyl peroxide.

It is preferable that the free-radical initiators used comprise water-soluble azo compounds.

Preference is also given to azo initiators, such as 2-tert-butylazo-2-cyanopropane, dimethyl azodiisobutyrate, azodiisobutyronitrile, 2-tert-butylazo-1-cyanocyclohexane, 1-tert-amylazo-1-cyanocyclohexane. Preference is also given to alkylperketals, such as 2,2-bis(tert-butylperoxy)butane, ethyl 3,3-bis(tert-butylperoxy)butyrate, 1,1-di(tert-butylperoxy)cyclohexane.

Particular preference is given to azo initiators, such as VAZO 52, VAZO 64 (AIBN), VAZO 67, VAZO 88, VAZO 44, VAZO 56, VAZO 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40, VF-096 1,1'-azobis(cyclohexane-1-carbonitrile), V-30 1-[(cyano-1-methylethyl)azo]formamide, VAm-110 2,2'-azobis(N-butyl-2-methylpropionamide), VAm-111 2,2'-azobis(N-cyclohexyl-2-methylpropionamide), VA-041 2,2'-azobis[2-(5-methyl-2-imidazolin-2-yl)propane] dihydrochloride, VA-044 2,2'-azobis[2-(2-imidazolin-2-yl)propane]dihydrochloride, VA-046B 2,2'-azobis[2-(2-imidazolin-2-yl)propanedisulfate dihydrates, V-50 2,2'-azobis(2-amidinopropane)hydrochloride, VA-057 2,2'-azobis[N-(2-carboxyethyl)-2-methylpropionamidine] tetrahydrate, VA-058 2,2'-azobis[2-(3,4,5,6-tetrahydropyrimidin-2-yl)propane]dihydrochloride, VA-060 2,2'-azobis{2-[1-(2-hydroxyethyl)-2-imidazolin-2-yl] propane}dihydrochloride, VA-061 2,2'-azobis[2-(2-imidazolin-2-yl)propane], VA-080 2,2'-azobis{2-methyl-N-[1,1-bis(hydroxymethyl)-2-hydroxyethyl]propionamide, VA-085 2,2'-azobis{2-methyl-N-[2-(1-hydroxybutyl)]propionamide}, VA-086 2,2'-azobis[2-methyl-N-(2-hydroxyethyl) propionamide]from Wako Chemicals.

Among the aluminum compounds, preference is given to metallic aluminum and aluminum salts having anions of the seventh main group, e.g. aluminum fluoride, aluminum fluoride trihydrate, aluminum chloride (anhydrous, crystallized; anhydrous, sublimed), aluminum chloride hexahydrate, aluminum hydroxychloride, ALCHLOR®-AC from Hardman Australia, basic aluminum chloride solution, aluminum chloride solution, sulfate-conditioned polyaluminum chloride solution (PACS) from Lurgi Lifescience, OBRAFLOC 18® from Oker Chemie GmbH, Alkaflock®, Ekocid® 60 grades, Sachtoklar® grades, Ekofloc®) grades, Ekozet grades from Sachtleben, Locron® and Parimal® grades from Clariant, anhydrous aluminum bromide, aluminum iodide, aluminum iodide hexahydrate.

Preference is given to aluminum salts having anions of the sixth main group, e.g. aluminum sulfide, aluminum selenide.

Preference is given to aluminum salts having anions of the fifth main group, e.g. aluminum phosphide, aluminum hypophosphite, aluminum antimonide, aluminum nitride, and also aluminum salts having anions of the fourth main group, e.g. aluminum carbide, aluminum hexafluorosilicate; and aluminum salts having anions of the first main group, e.g. aluminum hydride, aluminum calcium hydride, aluminum borohydride, or else aluminum salts of the oxo acids of the seventh main group, e.g. aluminum chlorate.

Preference is given to aluminum salts of the oxo acids of the sixth main group, e.g. aluminum sulfate, aluminum sulfate hydrate, aluminum sulfate hexahydrate, aluminum sulfate hexadecahydrate, aluminum sulfate octadecahydrate, aluminum sulfate solution from Ekachemicals, liquid aluminum sulfate from Oker Chemie GmbH, sodium aluminum sulfate, sodium aluminum sulfate dodecahydrate, aluminum potassium sulfate, aluminum potassium sulfate dodecahydrate, aluminum ammonium sulfate, aluminum ammonium sulfate dodecahydrate, magaldrate ($Al_5Mg_{10}(OH)_{31}(SO_4)_2 \times nH_2O$).

Preference is also given to aluminum salts of oxo acids of the fifth main group, e.g. aluminum nitrate nonahydrate, aluminum metaphosphate, aluminum phosphate, low-density aluminum phosphate hydrate, monobasic aluminum phosphate, monobasic aluminum phosphate solution; and aluminum salts of the oxo acids of the fourth main group, e.g. aluminum silicate, aluminum magnesium silicate, aluminum magnesium silicate hydrate (almasilate), aluminum carbonate, hydrotalcite ($Mg_6Al_2(OH)_{16}CO_3 * nH_2O$), dihydroxyaluminum sodium carbonate, $NaAl(OH)_2CO_3$, and aluminum salts of the oxo acids of the third main group, e.g. aluminum borate, or else aluminum salts of the pseudohalides, e.g. aluminum thiocyanate.

Preference is given to aluminum oxide (purum, purisimum, technical, basic, neutral, acidic), aluminum oxide hydrate, aluminum hydroxide, or mixed aluminum oxide hydroxide, and/or polyaluminum hydroxyl compounds, these preferably having an aluminum content of from 9 to 40% by weight.

Preferred aluminum salts are those having organic anions, e.g. aluminum salts of mono-, di-, oligo-, or polycarboxylic acids, e.g. aluminum diacetate, basic aluminum acetate, aluminum subacetate, aluminum acetotartrate, aluminum formate, aluminum lactate, aluminum oxalate, aluminum tartrate, aluminum oleate, aluminum palmitate, aluminum monosterarate, aluminum stearate, aluminum trifluoromethanesulfonate, aluminum benzoate, aluminum salicylate, aluminum hexaurea sulfate triiodide, aluminum 8-hydroxyquinolate.

Among the zinc compounds, preference is given to elemental, metallic zinc, and also to zinc salts having inorganic anions, e.g. zinc halides (zinc fluoride, zinc fluoride tetrahydrate, zinc chlorides (butter of zinc), bromides, zinc iodide).

Preference is given to zinc salts of the oxo acids of the third main group (zinc borate, e.g. Firebrake ZB, Firebrake 415, Firebrake 500), and also zinc salts of the oxo acids of the fourth main group (basic) zinc carbonate, zinc hydroxide carbonate, anhydrous zinc carbonate, basic zinc carbonate hydrate, (basic) zinc silicate, zinc hexafluorosilicate, zinc hexafluorosilicate hexahydrate, zinc stannate, zinc hydroxide stannate, zinc magnesium aluminum hydroxide carbonate), and zinc salts of the oxo acids of the fifth main group (zinc nitrate, zinc nitrate hexahydrate, zinc nitrite, zinc phosphate, zinc pyrophosphate); and zinc salts of the oxo acids of the sixth main group (zinc sulfate, zinc sulfate monohydrate, zinc sulfate heptahydrate), and zinc salts of the oxo acids of the seventh main group (hypohalites, halites, halates, e.g. zinc iodate, and perhalates, e.g. zinc perchlorate).

Preference is given to zinc salts of the pseudohalides (zinc thiocyanate, zinc cyanate, zinc cyanide).

Preference is given to zinc oxides, zinc peroxides (e.g. zinc peroxide), zinc hydroxides, or mixed zinc oxide hydroxides (standard zinc oxide, e.g. from Grillo, activated zinc oxide, e.g. from Rheinchemie, zincite, calamine).

Preference is given to zinc salts of the oxo acids of the transition metals (zinc chromate(VI) hydroxide (zinc yellow), zinc chromite, zinc molybdate, e.g. ™Kemgard 911 B, zinc permanganate, zinc molybdate-magnesium silicate, e.g. ™Kemgard 911 C).

Preferred zinc salts are those having organic anions, among which are zinc salts of mono-, di-, oligo-, and polycarboxylic acids, salts of formic acid (zinc formates), of acetic acid (zinc acetates, zinc acetate dihydrate, Galzin), of trifluoroacetic acid (zinc trifluoroacetate hydrate), zinc propionate, zinc butyrate, zinc valerate, zinc caprylate, zinc oleate, zinc stearate, of oxalic acid (zinc oxalate), of tartaric acid (zinc tartrate), citric acid (tribasic zinc citrate, dihydrate), benzoic acid (benzoate), zinc salicylate, lactic acid (zinc lactate, zinc lactate trihydrate), acrylic acid, maleic acid, succinic acid, of amino acids (glycine), of acidic hydroxy functions (zinc phenolate, etc), zinc para-phenolsulfonate, zinc para-phenolsulfonate hydrate, zinc acetylacetonate hydrate, zinc tannate, zinc dimethyldithiocarbamate, zinc trifluoromethanesulfonate.

Preference is given to zinc phosphide, zinc selenide, zinc telluride.

Among the titanium compounds are metallic titanium, and also titanium salts having inorganic anions, e.g. chloride, nitrate, or sulfate ions, or else having organic anions, e.g. formate or acetate ions. Particular preference is given to titanium dichloride, titanium sesquisulfate, titanium(IV) bromide, titanium(IV) fluoride, titanium(III) chloride, titanium (IV) chloride, titanium(IV) chloride tetrahydrofuran complex, titanium(IV) oxychloride, titanium(IV) oxychloride-hydrochloric acid solution, titanium(IV) oxysulfate, titanium(IV)oxysulfate-sulfuric acid solution, or else titanium oxides. Preferred titanium alkoxides are titanium(IV) n-propoxide (®Tilcom NPT, ®Vertec NPT), titanium(IV) n-butoxide, titanium chloride triisopropoxide, titanium(IV) ethoxide, titanium(IV) 2-ethylhexoxide (®Tilcom EHT, ®Vertetec EHT).

Among the tin compounds, preference is given to metallic tin, and also tin salts (stannous chloride, stannous chloride dihydrate, stannic chloride), and tin oxides, and stannic tert-butoxide as preferred tin alkoxide.

Among the zirconium compounds, preference is given to metallic zirconium and zirconium salts, such as zirconium (IV) chloride, zirconium sulfate, zirconium sulfate tetrahydrate, zirconyl acetate, zirconyl chloride, zirconyl chloride octahydrate. Further preferred compounds are zirconium oxides, and zirconium(IV) tert-butoxide, as preferred zirconium alkoxide.

The product mixture obtained after process stage a) is preferably reacted without further purification in process stage b) with the metal compounds.

Preference is given to the reaction in process stage b) in the solvent system provided via stage a).

The solvent system provided has preferably been modified when used in the reaction in process stage b). The preferred method of modifying the solvent system is addition of acidic components, solubilizers, foam inhibitors, etc.

In another embodiment of the process, the product mixture obtained after process stage a) is worked up.

In another embodiment of the process, the product mixture obtained after process stage a) is worked up and thereafter the dialkylphosphonic acids obtained after process stage a) and/or their alkali metal salts are reacted with the metal compounds in process stage b).

The product mixture is preferably worked up by isolating the dialkylphosphinic acids and/or their alkali metal salts.

The isolation step is preferably carried out via removal of the solvent system, e.g. via evaporative concentration.

The isolation step is preferably carried out via removal of the solvent system and of the ancillary components dissolved therein, e.g. via solid/liquid separation methods.

The product mixture is preferably worked up by removing insoluble by-products, e.g. via solid/liquid separation methods.

The subject matter of the present invention also in particular encompasses a process in which sodium hypophosphite is reacted with ethylene in the presence of sodium peroxodisulfate in water to give the sodium salt of diethylphosphinic acid as main product, and this product is then converted into diethylphosphinic acid, using sulfuric acid, and is reacted with aluminum hydroxide to give the aluminum salt of diethylphosphinic acid.

According to the invention, a diialkylphosphinic salt obtained in process stage a) is converted into the dialkylphosphinic acid, which is reacted with compounds of the metals Mg, Ca, Al, Zn, Ti, Sn, Zr, or Fe to give the dialkylphosphinic salts of these metals.

According to the invention, a dialkylphosphinic acid obtained in process stage a) is converted into a dialkylphosphinic salt, which is reacted with compounds of the metals Mg, Ca, Al, Zn, Ti, Sn, Zr, or Fe to give the dialkylphosphinic salts of these metals.

According to the invention, the dialkylphosphinic salt is isolated from the reaction mixture of stage b) via inventive solid/liquid separation methods. Inventive solid/liquid separation methods are sedimentation, hydrocyclone methods, filtering, and/or centrifuging.

The inventive dialkylphosphinic salts of metals Mg, Ca, Al, Zn, Ti, Sn, Zr, or Fe are dried.

Inventive drying assemblies are chamber driers, channel driers, belt driers (air velocity from 2 to 3 m/s), disc driers, (temperature from 20 to 400° C.), drum driers (hot gas temperature from 100 to 250° C.), paddle driers (temperature from 50 to 300° C.), pneumatic driers (air velocity from 10 to 60 m/s, exhaust air temperature from 50 to 300° C.), fluidized-bed driers (air velocity from 0.2 to 0.5 m/s, exhaust air temperature from 50 to 300° C.), cylinder driers, tubular driers (temperature from 20 to 200° C.), paddle driers, vacuum drying cabinets (temperature from 20 to 300° C., pressure from 0.001 to 0.016 MPa), vacuum-drum driers (temperature from 20 to 300° C., pressure from 0.004 to 0.014 MPa), vacuum paddle driers (temperature from 20 to 300° C., pressure from 0.003 to 0.02 MPa), vacuum conical driers (temperature from 20 to 300° C., pressure from 0.003 to 0.02 MPa).

The inventive dried dialkylphosphinic salts have a residual moisture level of from 0.01 to 10% by weight, preferably from 0.1 to 1% by weight.

The particle size of the inventive dialkylphosphinic salts is preferably from 0.1 to 1000 μm, particularly preferably from 10 to 100 μm.

The preferred bulk density of the inventive dialkylphosphinic salts is from 80 to 800 g/l, particularly preferably from 200 to 700 g/l.

The invention also provides the use, for preparation of flame retardants, of the metal dialkylphosphinates prepared by the inventive process.

In particular, the invention provides the use of the inventively prepared dialkylphosphinic salts of Mg, Ca, Al, Zn, Ti, Sn, Zr, or Fe for preparation of flame retardants for thermoplastic polymers, such as polyesters, polystyrene, or polyamide, and for thermoset polymers.

Suitable polyesters derive from dicarboxylic acids and from dialcohols, and/or from hydroxycarboxylic acids or from the corresponding lactones, e.g. polyethylene terephthalate, polybutylene terephthalate (Celanex 2500, Celanex 2002, Celanese; Ultradur, BASF), poly-1,4-dimethylolcyclohexane terephthalate, polyhydroxybenzoates, and also block polyether esters which derive from polyethers having hydroxy end groups; and polyesters modified with polycarbonates or with MBS.

Suitable polystyrenes are polystyrene, poly-(p-methylstyrene), and/or poly-(alpha-methylstyrene).

The suitable polystyrenes are preferably copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate, and styrene-butadiene-alkyl methacrylate, styrene-maleic anhydride, styrene-acrylonitrile-methyl acrylate; high-impact-systems mixtures composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

Suitable polystyrenes are preferably graft copolymers of styrene or alpha-methylstyrene, e.g. styrene on polybutadiene, styrene on polybutadiene-styrene copolymers, or styrene on polybutadiene-acrylonitrile copolymers, styrene and acrylonitrile (and, respectively, methacrylonitrile) on polybutadiene; styrene, acrylonitrile, and methyl methacrylate on polybutadiene; styrene and maleic anhydride on polybutadiene; styrene, acrylonitrile, and maleic anhydride or maleimide on polybutadiene; styrene and maleimide on polybutadiene, styrene and alkyl acrylates and, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, and also mixtures of these, e.g. those known as ABS polymers, MBS polymers, ASA polymers, or AES polymers.

Suitable polyamides and copolyamides derive from diamines and from dicarboxylic acids, and/or from aminocarboxylic acids, or from the corresponding lactams, for example nylon-4, nylon-6 (Akulon K122, DSM; Zytel 7301, DuPont; Durethan B 29, Bayer), nylon-6,6 (Zytel 101, DuPont; Durethan A30, Durethan AKV, Durethan AM, Bayer; Ultramid A3, BASF), −6,10, −6,9, −6,12, −4,6, −12, 12, nylon-11, and nylon-12 (Grillamid L20, Ems Chemie), aromatic polyamides based on m-xylene, diamine and adipic acid; polyamides prepared from hexamethylenediamine and iso- and/or terephthalic acid and, where appropriate, an elastomer as modifier, e.g. poly-2,4,4-trimethylhexamethyleneterephthalamide or poly-m-phenyleneisophthalamide. Other suitable polymers are block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol. EPDM- or ABS-modified polyamides or copolyamides are also suitable, as are polyamides condensed during processing ("RIM polyamide systems").

The inventive dialkylphosphinic salts are preferably used in compounded materials which are further used for the production of polymer moldings. A preferred process for production of polymer moldings is injection molding.

The examples below illustrate the invention in further detail.

EXAMPLE 1

Aluminum Diethylphosphinate 1500 g (14 mol) of sodium hypophosphite monohydrate and 35 g of concentrated sulfuric acid were dissolved in 7.5 kg of water and used as initial charge in a 16 l jacketed pressure reactor composed of enameled steel. Once the reaction mixture had been heated to 10° C., ethylene was introduced by way of a reducing valve set to 6 bar until saturation had been reached in the reactor. A solution of 80 g (5 mol %) of hydrogen peroxide (33% by weight) in 300 g of water was metered in uniformly over a period of 6 h with constant stirring at an ethylene pressure of 6 bar and a temperature of from 100 to 110° C. After a continued reaction time of 1 h, depressurization of the reactor, and cooling to about 90° C., 746 g (4.67 mol of aluminum) of aluminum acetate in 2254 g of water were added within a period of 60 min. The resultant solid was then filtered off, washed with 2 l of hot water, and vacuum-dried at 130° C. Yield: 1721 g (93.5% of theory).

| $^{31}$P NMR: | Al diethylphosphinate: | 97 mol % |
| --- | --- | --- |
| | Al butylethylphosphinate: | 2.5 mol % |
| | Al ethylphosphonate: | 0.5 mol % |

EXAMPLE 2

Aluminum Diethylphosphinate 1500 g (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 17 g (0.5 mol %) of sodium peroxodisulfate in 300 g of water was uniformly metered in over a period of 6 h with constant stirring, at an ethylene pressure of 6 bar and a temperature of from 100 to 110° C. After a continued reaction time of 1 h, depressurization of the reactor, and cooling to about 90° C., 3000 g (4.67 mol of aluminum) of a 46% strength aqueous solution of Al$_2$(SO$_4$)$_3$ 14H$_2$O were added over a period of 60 min. The resultant solid was then filtered off, washed with 2 l of hot water and vacuum-dried at 130° C. Yield: 1730 g (95% of theory).

| $^{31}$P NMR: | Al diethylphosphinate: | 98.6 mol % |
| --- | --- | --- |
| | Al ethylphosphonate: | 0.5 mol % |

EXAMPLE 3

Aluminum Diethylphosphinate 1500 g (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 20 bar until saturation had been reached in the reactor. A solution of 32 g (1 mol %) of ammonium peroxodisulfate in 300 g of water was uniformly metered in over a period of 6 h with constant stirring, at an ethylene pressure of 20 bar and a temperature of from 100 to 110° C. After a continued reaction time of 1 h, depressurization of the reactor, and cooling to about 90° C., 3000 g (4.67 mol of aluminum) of a 46% strength aqueous solution of Al$_2$(SO$_4$)$_3$ 14H$_2$O were added over a period of 60 min. The resultant solid was then filtered off, washed with 2 l of hot water and vacuum-dried at 130° C. Yield: 1750 g (95.1% of theory).

| $^{31}$P NMR: | Al diethylphosphinate: | 93.9 mol % |
| --- | --- | --- |
| | Al butylethylphosphinate: | 5.5 mol % |
| | Al ethylphosphonate: | 0.6 mol % |

EXAMPLE 4

Aluminum Diethylphosphinate 1500 g (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 19 g (0.5 mol %) of 2,2'-azobis(2-amidinopropane) hydrochloride (Wako Pure Chemical Industries, Ltd., grade V50 98.8%) in 300 g of water was uniformly metered in over a period of 6 h with constant stirring, at an ethylene pressure of 6 bar and a temperature of from 100 to 110° C. After a continued reaction time of 1 h, depressurization of the reactor, and cooling to about 90° C., 650 g (4.67 mol of aluminum) of aluminum chloride hexahydrate in 2350 g of water were added over a period of 60 min. The resultant solid was then filtered off, washed with 2 l of hot water and vacuum-dried at 130° C.

Yield: 1740 g (94.5% of theory).

| $^{31}$P NMR: | Al diethylphosphinate: | 97.7 mol % |
| --- | --- | --- |
| | Al butylethylphosphinate: | 1.6 mol % |
| | Al ethylphosphonate: | 0.7 mol % |

EXAMPLE 5

Aluminum Diethylphosphinate 1500 g (14 mol) of sodium hypophosphite monohydrate and 14 g of concentrated sulfuric acid were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 22 g (1 mol %) of sodium percarbonate in 300 g of water was metered in uniformly over a period of 6 h with constant stirring at an ethylene pressure of 6 bar and a temperature of from 100 to 110° C. After a continued reaction time of 1 h, depressurization of the reactor, and cooling to about 90° C., 3000 g (4.67 mol of aluminum) of a 46% strength aqueous solution of Al$_2$(SO$_4$)$_3$ 14H$_2$O were added over a period of 60 min. The resultant solid was then filtered off, washed with 2 l of hot water, and vacuum-dried at 130° C. Yield: 1706 g (92.7% of theory).

| $^{31}$P NMR: | Al diethylphosphinate: | 98.7 mol % |
|---|---|---|
| | Al butylethylphosphinate: | 0.8 mol % |
| | Al ethylphosphonate: | 0.5 mol % |

EXAMPLE 6

Aluminum Diethylphosphinate 1500 g (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 22 g (1 mol %) of sodium percarbonate and 16 g of tetraacetylethylenediamine in 300 g of water was uniformly metered in over a period of 6 h with constant stirring, at an ethylene pressure of 6 bar and a temperature of from 100 to 110° C. After a continued reaction time of 1 h, depressurization of the reactor, and cooling to about 90° C., 3000 g (4.67 mol of aluminum) of a 46% strength aqueous solution of $Al_2(SO_4)_3$ $14H_2O$ were added over a period of 60 min. The resultant solid was then filtered off, washed with 2 l of hot water and vacuum-dried at 130° C. Yield: 1720 g (93.4% of theory).

| $^{31}$P NMR: | Al diethylphosphinate: | 97.6 mol % |
|---|---|---|
| | Al butylethylphosphinate: | 1.8 mol % |
| | Al ethylphosphonate: | 0.6 mol % |

EXAMPLE 7

Aluminum Diethylphosphinate 1500 g (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 49 g (1 mol %) of dibenzoyl peroxide (70% by weight in water) in 300 g of water was uniformly metered in over a period of 6 h with constant stirring, at an ethylene pressure of 6 bar and a temperature of from 100 to 110° C. After a continued reaction time of 1 h, depressurization of the reactor, and cooling to about 90° C., 1725 g (4.67 mol of aluminum) of aluminum nitrate nonahydrate dissolved in 1275 g of water were added over a period of 60 min. The resultant solid was then filtered off, washed with 2 l of hot water and vacuum-dried at 130° C. Yield: 1697 g (92.2% of theory).

| $^{31}$P NMR: | Al diethylphosphinate: | 96.5 mol % |
|---|---|---|
| | Al butylethylphosphinate: | 2.7 mol % |
| | Al ethylphosphonate: | 0.8 mol % |

EXAMPLE 8

Aluminum Diethylphosphinate 1.5 kg (14 mol) of sodium hypophosphite monohydrate were dissolved in 7.5 kg of water and used as initial charge in a 16 l jacketed pressure reactor composed of enameled steel. Once the reaction mixture had been heated to 100° C., ethylene was introduced by way of a reducing valve set to 6 bar until saturation had been reached in the reactor. A solution of 33 g (1 mol %) of sodium peroxodisulfate in 300 g of water was uniformly metered in over a period of 6 h with constant stirring, at an ethylene pressure of 6 bar and a temperature of from 100 to 110° C. After a continued reaction time of 1 h, depressurization of the reactor, and cooling to about 90° C., 700 g of concentrated sulfuric acid were added over a period of 30 minutes. 364 g (4.67 mol) of aluminum hydroxide were then added and the mixture in the sealed reactor was heated to 150° C. for 8 h. After cooling to ambient temperature, the resultant solid was filtered off, washed with 2 l of hot water and vacuum-dried at 130° C. Yield: 1675 g (92% of theory).

| $^{31}$P NMR: | Al diethylphosphinate: | 98.7 mol % |
|---|---|---|
| | Al butylethylphosphinate: | 0.8 mol % |
| | Al ethylphosphonate: | 0.5 mol % |

EXAMPLE 9

(Comparison) Aluminum Diethylphosphinate 2.2 kg (20.7 mol) of sodium hypophosphite monohydrate were dissolved in 8 kg (7.62 l) of acetic acid and used as initial charge in a 16 l jacketed pressure reactor composed of enameled steel. Once the reaction mixture had been heated to 85° C., ethylene was introduced by way of a reducing valve set to 5 bar until saturation had been reached in the reactor. The reaction was initiated, with continuous stirring, via feed of a solution of 56 g (1 mol %) of 2,2'-azobis(2-amidinopropane) dihydrochloride in 250 ml of water, and the reaction was controlled by way of the free-radical initiator feed rate in such a way as to keep the reaction temperature in the reactor at 95° C. or below, with a jacket temperature of 80° C. and with continuous feed of ethylene at an average pressure of about 5 bar. The total feed time was 3 hours. The mixture was then allowed to continue reacting at 85° C. for a further 3 h. The reactor was depressurized and cooled to room temperature. The total weight of product was 11.7 kg. This corresponds to 1.2 kg of ethylene take-up (100% of theory).

800 g of the resultant mixture composed mainly of sodium diethylphosphinate were dissolved in 2500 ml of acetic acid, and 38 g (0.48 mol) of aluminum hydroxide were then added. The mixture was then heated at reflux for about 4 hours, cooled, and filtered. The resultant solid was washed first with 1 liter of glacial acetic acid, then with 1 liter of distilled water, and finally with 500 ml of acetone, and then vacuum-dried at 130° C. Yield: 183 g (92% of theory).

| NMR analysis: | Al diethylphosphinate: | 87.2 mol % |
|---|---|---|
| | Al ethylbutylphosphinate: | 11.9 mol % |
| | Al ethylphosphonate: | 0.9 mol % |

EXAMPLE 10

(Comparison): Aluminum Diethylphosphinate

A mixture of 2.64 kg (20 mol) of a 50% strength aqueous solution of hypophosphorous acid and 7 kg of acetic acid was charged in a 16 l jacketed pressure reactor made from enameled steel. Once the reaction mixture had been heated to 100° C., ethylene was introduced by way of a reducing valve set to 5 bar until saturation had been reached in the reactor. A solution of 56 g of 2,2'-azobis(N,N'-dimethyleneisobutyramidine)dihydrochloride in 500 g of acetic acid was fed uniformly into the mixture over a period of 6 h, with continuous stirring, at an ethylene pressure of 5 bar and a temperature of from 100 to 105° C. The solution obtained after a further reaction time of 1 h, depressurization of the reactor, and cooling to room temperature was very substantially freed from the acetic acid solvent on a rotary evaporator, and then treated with 10 l of water. Within a period of one hour, 4500 g (3.5 mol) of a 46% strength aqueous solution of $Al_2(SO_4)_3$ $14H_2O$ were added. The resultant solid was then filtered, washed twice with water, on each occasion using 2 l, and vacuum-dried at 130° C. Yield: 2520 g (82% of theory).

| NMR: | Al diethylphosphinate: | 90.8 mol % |
|------|------------------------|------------|
|      | Al butylethylphosphinate: | 8.4 mol % |
|      | Al ethylphosphonate:   | 0.8 mol %  |

EXAMPLE 11

The products prepared in examples 1 and 2 and in comparative examples 3 and 4 were mixed in a ratio by weight of 1:4 with polybutylene terephthalate (GRPBT; ®Celanex 2300 GV1/30; Celanese, USA) and incorporated at temperatures of from 230 to 260° C. in a twin-screw extruder (Leistritz LSM 30/34). The homogenized polymer strand was drawn off, cooled in a water bath, and then pelletized.

To assess polymer degradation, the solution viscosity (SV number) of the resultant polyester pellets was determined and compared with that of pure polyesters. The following results were obtained:

| Additive present | Purity* [%] | Viscosity number |
|------------------|-------------|------------------|
| Product of Example 2 | 98.6 | 1023 |
| Product of Example 8 | 98.7 | 1034 |
| Product of Example 9 (comparison) | 87.2 | 719 |
| Product of Example 10 (comparison) | 90.8 | 758 |
| No additive | — | 1072 |

*Based on the main component

The table illustrates the advantages of the inventively prepared products. The unitary, acetate-free inventive phosphinic salts reduce solution viscosities only slightly after incorporation into the polymer matrix, indicating almost unchanged molar mass. In contrast, the products prepared as in PCT/EP 98/07350 exhibit marked polymer degradation (greatly reduced viscosity numbers).

The invention claimed is:

1. A process for preparation of a dialkylphosphinic salt or a mixture of dialkylphosphinic salts comprising the steps of
   a) reacting, in a solvent system, at least one of hypophosphorous acid or a salt of hypophosphorous acid with at least one olefin in the presence of at least one free-radical initiator to give at least one of dialkylphosphinic acid or an alkali metal salt of dialkylphosphinic acid, and
   b) reacting the at least one of the dialkylphosphinic acid or the alkali metal salt of the dialkylphosphinic acid obtained in step a) with at least one of a metal or metal compound wherein the metal is selected from the group consisting of Mg, Ca, Al, Zn, Ti, Sn, Zr, and Fe, wherein the metal compound includes a metal selected from the group consisting of Mg, Ca, Al, Zn, Ti, Sn, Zr, and Fe to give at least one dialkylphosphinic salt of the metal, wherein the solvent system comprises at least one solvent system additive and water, wherein the solvent system comprises from 50 to 100% by weight of water and from 0 to 50% by weight of the at least one solvent system additive, wherein the at least one solvent system additive is selected from the group consisting of mineral acids, acidic salts, alkalis, and electrolytes, and wherein the mineral acids are selected from the group consisting of element-hydrogen acids, oxo acids, peroxo acids, and peroxo diacids of the elements of the seventh, sixth, fifth, fourth, or third main group of the periodic table.

2. The process as claimed in claim 1, wherein the solvent system comprises from 95 to 100% by weight of water and from 0 to 5% by weight of the at least one solvent system additive.

3. The process as claimed in claim 1, wherein the acidic salts are selected from the group consisting of sodium bisulfate, sodium bisulfite, and potassium bisulfite.

4. The process as claimed in claim 1, wherein the salt of hypophosphorous acid is an alkali metal salt.

5. The process as claimed in claim 4, wherein the alkali metal is sodium salt.

6. The process as claimed in claim 1, wherein step a) further comprises preparing the hypophosphorous acid in situ from a salt of hypophosphorous acid and from at least one mineral acid, where the ratio of additive acid to hypophosphite (based on equivalents) is from 0:1 to 2:1.

7. The process as claimed in one claim 1, wherein the at least one free-radical initiator is selected from the group consisting of peroxide-forming compounds and peroxo compounds.

8. The process as claimed in one claim 1, wherein the amount of the at least one free-radical initiator is from 0.001 to 10 mol %, based on the at least one of hypophosphorous acid and a salt of hypophosphorous acid.

9. The process as claimed in claim 7, wherein the at least one free-radical initiator is metered in at a rate of from 0.01 to 10 mol % of initiator per hour, based on the at least one of hypophosphorous acid and a salt of hypophosphorous acid.

10. The process as claimed in claim 1, wherein the at least one olefin is selected from the group consisting of ethylene, propylene, n-butene, isobutene, and mixtures thereof.

11. The process as claimed in claim 1, wherein the ratio of the at least one olefin to the at least one of hypophosphorous acid and a salt of hypophosphorous acid, on a molar basis is from 0:1 to 3:1.

12. The process as claimed in claim 1, wherein the reaction in step a) takes place at a pressure of from 1 to 100 bar of the at least one olefin.

13. The process as claimed in claim 1, wherein the atmosphere in step a) is composed of from 50 to 99.9% by weight of constituents of the solvent system and the at least one olefin.

14. The process as claimed in claim 1, wherein the atmosphere comprises at least one gaseous component which does not participate in the reaction, wherein the at least one gaseous component is selected from the group consisting of oxygen, nitrogen, carbon dioxide, noble gases, hydrogen, and alkanes.

15. The process as claimed in claim 1, wherein the reaction in step a) takes place at a temperature of from 0 to 250° C.

16. The process as claimed in claim 1, wherein the reaction in step a) takes place in an apparatus selected from the group consisting of absorption columns, spray towers, bubble columns, stirred tanks, mixer units and kneaders.

17. The process as claimed in claim 16, wherein the mixer units are selected from the group consisting of anchor stirrers, blade stirrers, MIG stirrers, propeller stirrers, impeller stirrers, turbine stirrers, trough stirrers, disperser discs, cavitation stirrers, rotor-stator mixers, static mixers, Venturi nozzles, and mammoth pumps.

18. The process as claimed in claim 1, further comprising mixing the at least olefin, the at least one free-radical initiator, the solvent system, and the at least one of hypophosphorous acid and a salt of hypophosphorous acid, and wherein the mixing produces a mixing intensity corresponding to a rotations Reynolds number of from 1 to 1 000 000.

19. The process as claimed in claim 1, wherein step a) further comprises mixing the at least olefin, the at least one free-radical initiator, the solvent system, and the at least one of hypophosphorous acid and a salt of hypophosphorous acid, and wherein the energy produced by the mixing is from 0.083 to 10 kW/m$^3$.

20. The process as claimed in claim 1, wherein the reaction of step b) takes place, for tetravalent metal ions or metals with a stable tetravalent oxidation state, molar ratio of dialkylphosphinic acid/dialkylphosphinic salt to metal of from 6:1 to 1:0.66.

21. The process as claimed in claim 1, wherein the reaction of step b) takes place, for trivalent metal ions or metals with a stable trivalent oxidation state, at a molar ratio of dialkylphosphinic acid/dialkylphosphinic salt to metal of from 4.5:1 to 1:0.66.

22. The process as claimed in claim 1, wherein the reaction of step b) takes place, for divalent metal ions or metals with a stable divalent oxidation state, at a molar ratio of dialkylphosphinic acid/dialkylphosphinic salt to metal of from 3:1 to 1:0.66.

23. The process as claimed in claim 1, wherein the reaction of step b) takes place, for monovalent metal ions or metals with a stable monovalent oxidation state, at a molar ratio of dialkylphosphinic acid/dialkylphosphinic salt to metal of from 1.5:1 to 1:0.66.

24. The process as claimed in claim 1, wherein the at least one metal compound is selected from the group consisting of metal oxides, metal hydroxides, metal oxide hydroxides, metal borates, metal carbonates, metal hydroxocarbonates, metal hydroxocarbonate hydrates, mixed metal hydroxocarbonates, mixed metal hydroxocarbonate hydrates, metal phosphates, metal sulfates, metal sulfate hydrates, metal hydroxosulfate hydrates, mixed metal hydroxosulfate hydrates, oxysulfates, metal acetates, metal nitrates, metal fluoride, metal fluoride hydrates, metal chloride, metal chloride hydrates, metal oxychlorides, metal bromides, metal iodides, metal iodide hydrates, metal derivatives of a carboxylic acid, and/or metal alkoxides, and mixtures thereof.

25. The process as claimed in claim 1, wherein the metal compound is selected from the group consisting of aluminum chloride, aluminum hydroxide, aluminum nitrate, aluminum sulfate, titanyl sulfate, zinc sulfate and mixtures thereof.

26. The process as claimed in claim 1, wherein the reaction of step b) takes place at a temperature of from 20 to 250° C.

27. The process as claimed in claim 1, wherein the reaction of step b) takes place at a pressure of from 1 Pa to 200 MPa.

28. The process as claimed in claim 1, wherein the reaction time of step b) is from $1*10^{-7}$ to $1*10^2$ h.

29. The process as claimed in claim 1, wherein the solids content of the at least one dialkylphosphinic salt of the metal is from 0.1 to 70% by weight.

30. The process as claimed in claim 1, wherein the reaction in step b) takes place in a stirred tank, mixer, kneader or combination thereof.

31. The process as claimed in claim 1, wherein the amount of energy introduced in step b) is from 0.083 to 1.65 kW/m$^3$.

32. The process as claimed in claim 1, wherein, in step a) the at least one dialkylphosphinic acid or an alkali metal salt of dialkylphosphinic acid is converted into the respective other compound in order to obtain a uniform product, before step b) begins.

33. The process as claimed in claim 1, wherein step a) further comprises converting the alkali metal salt of the diakylphosphinic acid into the dialkylphosphinic acid.

34. The process as claimed in claim 1, wherein step a) further comprises converting the dialkylphosphinic acid to the alkali metal salt of the diakylphosphinic acid.

35. The process as claimed in claim 1, wherein step b) further comprises isolating the at least one dialkylphosphinic salt of the metal from the reaction mixture by at least one of filtration or centrifuging.

36. The process as claimed in claim 1, wherein step b) further comprises isolating the at least one diethylphosphinic salt of the metal from the reaction mixture using at least one of pressure filter funnels, vacuum filter funnels, filter funnels with stirrer, pressurized candle filters, axial leaf filters, circular leaf filters, centrifugal leaf filters, chamber/frame filter presses, automatic chamber filter presses, vacuum multicompartment drum filters, vacuum multicompartment leaf filters, vacuum top-feed filters, vacuum horizontal-table filters, rotation pressure filters, or vacuum belt filters.

37. The process as claimed in claim 35, wherein the filtration pressure is from 0.5 Pa to 6 MPa.

38. The process as claimed in claim 35, wherein the filtration temperature is from 0 to 400° C.

39. The process as claimed in claim 35, wherein the specific filter rate is from 10 to 200 $kg*h^{-1}*m^{-2}$.

40. The process as claimed in claim 35, wherein the residual moisture level of the cake is from 5 to 60%.

41. The process as claimed in claim 1, wherein step b) further comprises isolating the at least one diethylphosphinic salt of the metal using at least one of solid-wall centrifuges, plough centrifuges, chamber centrifuges, helical-conveyor centrifuges, disc centrifuges, tube centrifuges, sieve centrifuges, screen-conveyor centrifuges, screen-plough centrifuges, or reciprocating-conveyor centrifuges.

42. The process as claimed in claim 35, wherein the centrifugal force ratio is from 300 to 15 000.

43. The process as claimed in claim 35, wherein the suspension throughput rate is from 2 to 400 $m^3*h^{-1}$.

44. The process as claimed in claim 35, wherein the solids throughput rate is from 5 to 80 $t*h^{-1}$.

45. The process as claimed in claim 35, further comprising drying the at least one diethylphosphinic salt of the metal after the isolating step.

46. The process as claimed in claim 45, wherein the at least one dialkylphosphinic salt of the metal has a residual moisture level of from 0.01 to 10% by weight after the drying step.

47. The process as claimed in claim 1, wherein the at least one dialkylphosphinic salt of the metal has an average particle size of from 0.1 to 2000 µm.

48. The process as claimed in claim 1, wherein the at least one dialkylphosphinic salt of the metal has a bulk density of from 80 to 800 g/l.

49. A process for preparation of a dialkylphosphinic salt or a mixture of dialkylphosphinic salts comprising the steps of:
  a) reacting, in a solvent system, at least one of hypophosphorous acid or a salt of hypophosphorous acid with an olefin in the presence of at least one free-radical initiator to give at least one dialkylphosphinic compound selected from the group consisting of a dialkylphosphinic acid and an alkali metal salt of dialkylphosphinic acid, wherein the solvent system comprises at least one solvent system additive and water, wherein the solvent system comprises from 50 to 100% by weight of water and from 0 to 50% by weight of the at least one solvent system additive, wherein the at least one solvent system additive is selected from the group consisting of mineral acids, acidic salts, alkalis, and electrolytes, and wherein the mineral acids are selected from the group consisting of element-hydrogen acids, oxo acids, peroxo acids, and peroxo diacids of the elements of the seventh, sixth, fifth, fourth, or third main group of the periodic table,
  a1) converting the at least one dialkylphosphinic compound obtained in step a) mutually into one another and
  b) reacting the at least one dialkylphosphinic compound obtained in step a1) with at least one metal compound, wherein the at least one metal compound includes a metal selected from the group consisting of Mg, Ca, Al, Zn, TI, Sn, Zr, or Fe to give at least one dialkylphosphinic salt of the metal.

50. A process for preparation of a dialkylphosphinic salt or a mixture of dialkylphosphinic salts comprising the steps of
  a) reacting, in a solvent system, at least one of hypophosphorous acid or a salt of hypophosphorous salt with at least one olefin in the presence of at least one free-radical initiator to give at least one of a dialkylphosphinic acid or a alkali metal salt of dialkylphosphinic acid, wherein the solvent system comprises at least one solvent system additive and water, wherein the solvent system comprises from 50 to 100% by weight of water and from 0 to 50% by weight of the at least one solvent system additive, wherein the at least one solvent system additive is selected from the group consisting of mineral acids, acidic salts, alkalis, and electrolytes, and wherein the mineral acids are selected from the group consisting of element-hydrogen acids, oxo acids, peroxo acids, and peroxo diacids of the elements of the seventh, sixth, fifth, fourth, or third main group of the periodic table, and
  b) reacting the at least one of a dialkylphosphinic acid or an alkali metal of dialkylphosphinic acid with at least one compound, wherein the at least one compound includes a metal selected from the group consisting of Mg, Ca, Al, Zn, Ti, Sn, Zr, and Fe to give at least one dialkylphosphinic salt of the metal.

51. The process as claimed in claim 49, further comprising
  from 10 to 100% by weight of the at least one dialkylphosphinic acid or alkali metal salt of dialkylphosphinic acid, and
  from 10 to 100% by weight of the solvent system,
  the entirety being 100% by weight.

52. The process as claimed in claim 1, wherein the solvent system comprises from 80 to 100% by weight of water and from 0 to 20% by weight of the at least one solvent additive.

53. The process as claimed in claim 7, wherein the peroxo compounds are selected from the group consisting of hydrogen peroxide, potassium persulfate, sodium persulfate, ammonium persulfate, and azo compounds.

54. The process as claimed in claim 53, wherein the azo compounds are selected from the group consisting of 2,2'-azobis(2-amidinopropane) dihydrochloride and 2,2'-azobis(N,N'-dimethyleneisobutyramidine)dihydrochloride.

55. The process as claimed in claim 11, wherein the ratio of the at least one olefin to the at least one of hypophosphorous acid and a salt of hypophosphorous acid, on a molar basis is from 0.5:1 to 2.5:1.

56. The process as claimed in claim 1, wherein the reaction in step a) takes place at a pressure of from 2 to 50 bar of the at least one olefin.

57. The process as claimed in claim 1, wherein the atmosphere in step a) is composed of from 70 to 95% by weight of constituents of the additive solvent system and the at least one olefin.

58. The process as claimed in claim 1, wherein the reaction in step a) takes place at a temperature of from 20 to 200° C.

59. The process as claimed in claim 1, wherein the reaction in step a) takes place at a temperature of from 50 to 150° C.

60. The process as claimed in claim 1, further comprising mixing the reaction solution in step a) and wherein the reaction solution experiences a mixing intensity corresponding to a rotations Reynolds number of from 100 to 100 000.

61. The process as claimed in claim 7, wherein step a) further comprises mixing the at least olefin, the at least one free-radical initiator, the additive solvent system, and the at least one of hypophosphorous acid and a salt of hypophosphorous acid, and wherein the energy introduced by the mixing is from 0.33 to 1.65 kW/m$^3$.

62. The process as claimed in claim 1, wherein the reaction of step b) takes place at a temperature of from 80 to 120° C.

63. The process as claimed in claim 1, wherein the reaction of step b) takes place at a pressure of from 0.01 MPa to 10 MPa.

64. The process as claimed in claim 1, wherein the solids content of the dialkylphosphinic salts of the metal is from 5 to 40% by weight.

65. The process as claimed in claim 1, wherein the amount of energy introduced in step b) is from 0.33 to 1.65 kW/m$^3$.

66. The process as claimed in claim 45, wherein the at least one dialkylphosphinic salt of the metal has a residual moisture level of from 0.1 to 1% by weight after the drying step.

67. The process as claimed in claim 1, wherein the at least one dialkylphosphinic salt of the metal has an average particle size of from 10 to 500 μm.

68. The process as claimed in claim 1, wherein the at least one dialkylphosphinic salt of the metal has a bulk density of from 200 to 700 g/l.

69. The process as claimed in claim 50, further comprising
  from 10 to 100% by weight of the at least one dialkylphosphinic acid or alkali metal salt of dialkylphosphinic acid, and
  from 10 to 100% by weight of the solvent system,
  the entirety being 100% by weight.

* * * * *

UNITED STATES PATENT AND TRADEMARK OFFICE
CERTIFICATE OF CORRECTION

PATENT NO.      : 7,635,785 B2                                  Page 1 of 1
APPLICATION NO. : 11/016663
DATED           : December 22, 2009
INVENTOR(S)     : Harald Bauer et al.

It is certified that error appears in the above-identified patent and that said Letters Patent is hereby corrected as shown below:

On the Title Page (73) Assignee should read: Clariant Produkte (Deutschland) GmbH, Sulzbach (DE)

Signed and Sealed this
Twelfth Day of May, 2015

Michelle K. Lee
*Director of the United States Patent and Trademark Office*